(12) United States Patent
Lim et al.

(10) Patent No.: US 7,405,077 B2
(45) Date of Patent: Jul. 29, 2008

(54) SPERM PROTEIN 17 FOR THE DIAGNOSIS AND TREATMENT OF CANCER

(75) Inventors: Seah H. Lim, Amarillo, TX (US); Maurizio Chiriva-Internati, Amarillo, TX (US); Zhiqing Wang, Amarillo, TX (US)

(73) Assignee: Albany Medical College, Albany, NY (US)

( * ) Notice: Subject to any disclaimer, the term of this patent is extended or adjusted under 35 U.S.C. 154(b) by 518 days.

(21) Appl. No.: 10/082,959

(22) Filed: Feb. 26, 2002

(65) Prior Publication Data

US 2002/0168662 A1    Nov. 14, 2002

Related U.S. Application Data

(60) Provisional application No. 60/271,516, filed on Feb. 26, 2001.

(51) Int. Cl.
    C12N 5/08    (2006.01)
(52) U.S. Cl. .................................... 435/372.3
(58) Field of Classification Search ............... 435/325, 435/372.3, 320.1, 7.1, 7.23; 536/23.1, 23.5, 536/24.3, 24.33
    See application file for complete search history.

(56) References Cited

U.S. PATENT DOCUMENTS

| | | | |
|---|---|---|---|
| 5,480,799 A | 1/1996 | O'Rand et al. | 435/252.3 |
| 5,616,322 A | 4/1997 | O'Rand et al. | 424/192.1 |
| 5,695,994 A | 12/1997 | Boon-Falleur et al. | 435/325 |
| 5,814,456 A | 9/1998 | O'Rand et al. | 435/7.1 |
| 5,820,861 A | 10/1998 | O'Rand et al. | 424/184.1 |
| 5,962,318 A | 10/1999 | Rooney et al. | 435/325 |
| 5,980,896 A | 11/1999 | Hellstrom et al. | 424/183.1 |
| 6,083,751 A | 7/2000 | Feldhaus et al. | 435/372.3 |
| 6,165,725 A | 12/2000 | Van Buren et al. | 435/6 |
| 6,171,796 B1 | 1/2001 | An et al. | 435/6 |

FOREIGN PATENT DOCUMENTS

| | | |
|---|---|---|
| WO | WO 95/15764 | 6/1995 |
| WO | WO 97/39020 | 10/1997 |

OTHER PUBLICATIONS

Chiriva-Internati et al, Blood, 2000, 96:11:272b.*
Lefkovits, Immunology Methods Manual. The Comprehensive Sourcebook of Techniques, vol. 3., 1997, pp. 1670-1673.*
Buchli et al (BBA, 2002, 1578:29-42).*
O'Rand et al., "Identification of Sperm Antigen Targets for Immunocontraception: B-Cell Epitope Analysis of Sp17," Reprod. Fertil. Dev., 6, 289-96 (1994).
Lim et al., "Sperm protein 17 is a novel cancer-testis antigen in multiple myeloma," Blood, vol. 97, No. 5, 1508-1510 (2001).
Chiriva-Internati et al., "Sperm protein 17 (Sp17) in multiple myeloma: opportunity for myeloma-specific donor T cell infusion to enhance graft-versus myeloma effect without increasing graft-versus-host disease risk," Eur. J. Immunol, 31: 2277-2283 (2001).
Lea et al., "Cloning and sequencing of cDNAs encoding the human sperm protein Sp17," Biochimica et Biophysica Acta 1307, 263-266 (1996).
Lea et al., "Autoimmunogenicity of the human sperm protein Sp17 in vasectomized men and identification of linear B cell epitopes," Fertility and Sterility, vol. 67, No. 2, 355-361 (1997).

\* cited by examiner

*Primary Examiner*—Susan Ungar
(74) *Attorney, Agent, or Firm*—Heslin Rothenberg Farley & Mesiti P.C.; Charles E. Bell; Kathy Smith Dias

(57) ABSTRACT

The results herein identify Sp17 as a novel cancer-testis antigen in multiple myeloma. Sp17 recombinant protein was generated from *E. coli*. A CD8 predominant CTL line was generated that was able to lyse autologous targets in a Sp17-dependent HLA class I-restricted manner, using dendritic cells as the antigen-presenting cells and DOTAP to deliver the Sp17 protein to the dendritic cells. A combination of HLA-matched and mismatched antibody-enriched fresh myeloma tumor cells and myeloma cell lines were used as targets for the recombinant protein-propagated CTL. The findings of target cell lysis suggest that the Sp17 protein produced by Sp17+ tumor cells are processed and presented in vivo and that the CTL epitopes are presented in association with HLA class I molecules in a concentration and configuration recognized by recombinant protein-propagated CTL.

1 Claim, No Drawings

SPERM PROTEIN 17 FOR THE DIAGNOSIS AND TREATMENT OF CANCER

This application claims priority of U.S. Provisional Patent Application No. 60/271,516, filed Feb. 26, 2001 now abandoned.

This invention was made with support from the National Institutes of Health, National Cancer Institute, Grant No. RO1 CA88434-01. The U.S. Government may have certain rights in this invention.

FIELD OF THE INVENTION

The present invention relates generally to the identification of sperm protein 17 as a cancer-testis antigen which is expressed aberrantly by tumor cells, and more particularly to the resultant use of sperm protein 17 for the diagnosis and treatment of cancer.

BACKGROUND OF THE INVENTION

Throughout this application various publications are referenced, many in parenthesis. Full citations for each of these publications are provided at the end of the Detailed Description and throughout the Detailed Description. The disclosures of each of these publications in their entireties are hereby incorporated by reference in this application.

Biological therapy (sometimes called immunotherapy, biotherapy, or biological response modifier therapy) is a relatively new addition to the family of cancer treatments that also includes surgery, chemotherapy, and radiation therapy. Biological therapies use the body's immune system, either directly or indirectly, to fight cancer or to lessen the side effects that may be caused by some cancer treatments.

The immune system is a complex network of cells and organs that work together to defend the body against attacks by "foreign," or "non-self," invaders. This network is one of the body's main defenses against disease. It works against disease, including cancer, in a variety of ways. For example, the immune system may recognize the difference between healthy cells and cancer cells in the body and work to eliminate those that become cancerous. Cancer may develop when the immune system breaks down or is not functioning adequately. Biological therapies are designed to repair, stimulate, or enhance the immune system's responses.

Immune system cells include lymphocytes and monocytes. Lymphocytes are a type of white blood cell found in the blood and many other parts of the body. Types of lymphocytes include B cells, T cells, and Natural Killer cells. B cells (B lymphocytes) mature into plasma cells that secrete antibodies (immunoglobulins), the proteins that recognize and attach to foreign substances known as antigens. Each type of B cell makes one specific antibody, which recognizes one specific antigen. T cells (T lymphocytes) directly attack infected, foreign, or cancerous cells. T cells also regulate the immune response by signaling other immune system defenders. T cells work primarily by producing proteins called lymphokines. Natural Killer cells (NK cells) produce powerful chemical substances that bind to and kill any foreign invader. They attack without first having to recognize a specific antigen. Monocytes are white blood cells that can swallow and digest microscopic organisms and particles in a process known as phagocytosis. Monocytes can also travel into tissue and become macrophages.

Cells in the immune system secrete two types of proteins: antibodies and cytokines. Antibodies respond to antigens by latching on to, or binding with, the antigens. Specific antibodies match specific antigens. Cytokines are substances produced by some immune system cells to communicate with other cells. Types of cytokines include lymphokines, interferons, interleukins, and colony-stimulating factors. Cytotoxic cytokines are released by a type of T-cell called a cytotoxic T-cell (CTL). These cytokines attack cancer cells directly.

Cancer vaccines are a form of biological therapy currently under study. Vaccines for infectious diseases, such as measles, mumps, and tetanus, are effective because they expose the body's immune cells to weakened forms of antigens that are present on the surface of the infectious agent. This exposure causes the immune cells to produce more plasma cells, which make antibodies. T-cells that recognize the infectious agent also multiply. These activated T-cells later remember the exposure. The next time the agent enters the body, cells in the immune system are already prepared to respond and stop the infection.

For cancer treatment, researchers are developing vaccines that may encourage the patient's immune system to recognize cancer cells. These vaccines may help the body reject tumors and prevent cancer from recurring. Cancer vaccines given when the tumor is small may be able to eradicate the cancer. Early cancer vaccine clinical trials involved mainly patients with melanoma. Currently, cancer vaccines are also being studied in the treatment of many other types of cancer, including lymphomas and cancers of the kidney, breast, ovary, prostate, colon, and rectum.

Multiple myeloma (MM) is one form of cancer. Allogeneic stem cell transplantation has been applied to patients with multiple myeloma (MM) to induce disease remission, but many patients still experience disease relapse and die of the disease. There is a strong correlation between graft-versus-host disease (GVHD) and graft-versus-myeloma (GVM) in MM patients, so those patients who develop GVHD have a lower risk of disease relapse (Desikan et al. 2000). This observation suggests that the GVM effect of stem cell transplantation may be part of the more global GVH reactions due to minor histocompatibility differences between the donor and the recipient. Therefore, GVM is achieved at the expense of GVHD. As a result, although these patients have a lower risk of disease relapse, such advantage may not be translated into improved survival because a high proportion of these patients die due to complications associated with GVHD. If a myeloma antigen can be specifically targeted, tumor-specific donor CTL could be generated and administered to these patients following T cell-depleted allogeneic stem cell transplantation to enhance the GVM effect without inducing GVHD. The myeloma idiotypic protein is clone specific and has been previously used in the autologous settings (Lim and Bailey-Wood 1999; Wen et al. 1998; Reichardt et al. 1999; Massaia et al. 1999; Osterborg et al. 1999). However, the clinical results in the autologous settings have been disappointing due probably to the weak immunogenicity of the idiotypes and low effector:target ratio generated by the vaccines.

Therefore, there is a need for studies into other novel tumor antigens in MM that elicit consistent and strong tumor-specific immune responses that produce effective antitumor effects.

In addition to the idiotypes, T lymphocyte targets on myeloma cells that may be suitable molecules for enhancement of GVM without inducing GVHD include MUC-1 (Noto et al. 1997), mutant ras oncogene protein (Corradini et al. 1993) and the new class of tumor antigens, known as CT (cancer-testis) antigens (Olds and Chen 1998). The CT antigens include members of the MAGE family, BAGE, GAGE and NY-ESO-1. They are normal testicular antigens expressed aberrantly in tumor cells. Their restricted normal tissue expression makes them ideal molecules for immune targeting. CT antigens are expressed in some myeloma cells (Lim et al. 1999; Van Varen et al. 1999). Anti-MAGE-A3 CTL clones raised from normal healthy donors could lyse myeloma cells in an HLA-A1- and HLA-A2-specific manner (Van Baren et al. 1999).

Sp17 is a protein of apparent molecular mass of 24.5 kDa that is involved in acrosome reactions in spermatozoa. It has, in the last few years, been the target of investigation as an immunocontraceptive. It is a highly immunogenic protein in vivo, and previous studies have shown a high incidence for the spontaneous development of autoantibodies against Sp17 in vasectomized normal healthy males (Lea et al. 1997). Both B and T cell epitopes of Sp17 have also been defined in mice (Lea et al. 1998).

SUMMARY OF THE INVENTION

Various studies have demonstrated the aberrant expression of normal testicular proteins in neoplastic cells. These proteins collectively form the new class of tumor antigens called cancer-testis (CT) antigens. Their selective normal tissue expression makes them ideal antigens for immune targeting of the malignant disease. In this study, the expression of a spermatozoa protein, Sp17, in multiple myeloma was investigated. It was found that Sp17 is detectable in tumor cells from 12 of 47 (26%) myeloma patients. Reverse transcription polymerase chain reaction (RT-PCR) and Western blot analysis detected Sp17 transcripts and proteins, respectively. Northern blot analysis and RT-PCR demonstrated that Sp17 transcripts were detected only in normal testis, supporting its tissue specificity. Since a high proportion of normal individuals develop antibodies against Sp17 following vasectomy, Sp17 is likely to be a highly immunogenic protein in vivo.

Sp17 is therefore a novel member of the CT antigen family and is an ideal target for immunotherapy of multiple myeloma through the generation of donor CTL against tumor cells in MM. MM patients undergo a T cell depleted allogeneic stem cell transplantation to reduce transplant-related toxicities and GVHD. Following donor hemapoeitic engraftment, donor-derived Sp17-specific CTL are administered to these patients at regular intervals to enhance GVM without inducing GVHD. As discussed further below, recombinant Sp17 protein was produced and used with autologous dendritic cells (DC) to generate Sp17-specific HLA class I-restricted CTL from the peripheral blood lymphocytes of a previously unvasectomized healthy male donor. These CTL were able to lyse autologous Epstein-Barr virus-transformed lymphoblastoid cells in a Sp17-dependent manner. Target lysis was HLA-A1 and HLA-B27 restricted. Cytoxicity could be blocked by antibodies against monomorphic HLA class I, HLA-A1 and HLA-B27 molecules but not HLA class II molecules. Most importantly, the CTL lysed HLA class I-matched Sp17-positive tumor cells, suggesting that Sp17 is processed and presented in association with the HLA class I molecules in Sp17-positive tumor cells in a concentration and configuration that can be recognized by recombinant protein-primed CTL. Analysis by flow cytometry of the CTL indicated that they were predominantly CD8 in phenotype and they produced Interferon-γ (IFN-γ) and very little Interleukin-4 (IL-4). These results evidence the utility for the generation and administration of donor-derived Sp17-specific CTL to augment GVM without inducing GVHD following allogeneic stem cell transplant for MM.

Based on these results, the subject invention thus provides a method for determining regression or progression of cancer in a patient previously diagnosed with cancer. The method comprises assaying a sample of the patient previously diagnosed with cancer for current level of expression of a nucleic acid molecule which encodes Sp17, and comparing the current level of expression to a prior level of expression of Sp17 in the patient, variation therebetween indicating progression or regression of the cancer.

The invention further provides a method for generating Sp-17-specific immune effector cells ex vivo which comprises pulsing antigen presenting cells with recombinant Sp-17 or antigenic portions thereof; and contacting the pulsed antigen presenting cells with immune effector cells for a time sufficient to stimulate Sp-17-reactive immune effector cells under conditions permissive for proliferation of Sp17-reactive immune effector cells, whereby Sp17-specific immune effector cells are thereby generated. In one embodiment, the antigen presenting cells are dendritic cells and the immune effector cells are cytotoxic T lymphocytes.

Further provided are ex vivo antigen presenting cells that present Sp-17 antigens for class I MHC, wherein the antigen presenting cells have had recombinant Sp17 or antigenic portions thereof introduced into them in a manner effective to antigenically present the Sp-17 antigen for class I MHC, as well as an isolated cytotoxic T cell line which specifically recognizes Sp-17.

Additionally provided is a method of treating a subject suffering from cancer characterized by cells having Sp17 on the cell surface. The method comprises administering to the subject an effective amount of the cytotoxic T cell line.

A method of diagnosing cancer in a subject is provided. The method comprises obtaining a test sample from a subject and determining level of expression of a nucleic acid molecule which encodes Sp17 in the test sample; and comparing the level of expression to level of expression of Sp17 in a control sample from another subject known not to have cancer; wherein a greater level of expression in the test sample as compared to the level of expression in the control sample is diagnostic of cancer. In one embodiment, the level of expression is determined using an antibody specifically immunoreactive with Sp17.

The invention further provides an immunoconjugate comprising an Sp-17 antigen-binding agent and a therapeutic agent. The therapeutic agent can be selected from the group consisting of an anti-tumor agent, a cytotoxin, a radioactive agent, an antibody, and an enzyme, and the Sp-17 antigen-binding agent can be provided as a monoclonal antibody specifically immunoreactive with Sp-17.

Also provided is a method of treating a subject suffering from cancer characterized by cells having Sp17 on the cell surface, which comprises administering to the subject an effective amount of the immunoconjugate such that the immunoconjugate binds to the Sp17 on the cells' surface via the Sp-17 antigen-binding agent and the therapeutic agent kills the cells, thereby treating the subject. A method for selectively killing tumor cells expressing Sp-17 comprises reacting the immunoconjugate with the tumor cells.

A method for imaging cancer cells characterized by having Sp-17 on the cell surface, comprises administering to a patient a detectably labeled Sp-17 antigen-binding agent in an amount effective for binding to Sp-17 present on cells in the patient, and detecting the bound detectably labeled Sp-17 antigen-binding agent, thereby imaging the cancer cells characterized by having Sp-17 on the cell surface. The detectably labeled Sp-17 antigen-binding agent can be a labeled monoclonal antibody specifically immunoreactive with Sp-17.

DETAILED DESCRIPTION OF THE INVENTION

As used herein, an "immunoconjugate" means any molecule or ligand such as an antibody or growth factor chemically or biologically linked to a cytotoxin, a radioactive agent, an anti-tumor drug or a therapeutic agent. The antibody or growth factor may be linked to the cytotoxin, radioactive agent, anti-tumor drug or therapeutic agent at any location along the molecule so long as it is able to bind its target. Examples of immunoconjugates include immunotoxins and antibody conjugates.

As used herein, "selectively killing" means killing those cells to which the antibody binds.

As used herein, "immunotoxin" means an antibody or growth factor chemically or biologically linked to a cytotoxin or cytotoxic agent.

As used herein, an "effective amount" is an amount of the antibody, immunoconjugate, recombinant molecule which kills cells or inhibits the proliferation thereof.

As used herein, "antigen-binding region" means that part of the antibody, recombinant molecule, the fusion protein, or the immunoconjugate of the invention which recognizes the target or portions thereof.

As used herein, "therapeutic agent" means any agent useful for therapy including anti-tumor drugs, cytotoxins, cytotoxin agents, and radioactive agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, "a radioactive agent" includes any radioisotope which is effective in destroying a tumor. Examples include, but are not limited to, cobalt-60 and X-rays. Additionally, naturally occurring radioactive elements such as uranium, radium, and thorium which typically represent mixtures of radioisotopes, are suitable examples of a radioactive agent.

As used herein, "administering" means oral administration, administration as a suppository, topical contact, intravenous, intraperitoneal, intra muscular or subcutaneous administration, or the implantation of a slow-release device such as a miniosmotic pump, to the subject.

As used herein "reacting" means to recognize and bind the target. The binding may be non-specific. Specific binding is preferred.

As used herein, the term "antigen presenting cell" refers to an immune accessory cell that participates in antigen-inductive events, and includes mononuclear phagocytes, dendritic cells, and B cells, which express high levels of class I MHC. Autologous antigen presenting cells are antigen presenting cells obtained from the same donor as the effector cells. Alternatively, class I MHC-matched antigen presenting cells from a different donor can be used with autologous T cells. Transduced antigen presenting cells refer to antigen presenting cells that have been effectively transfected or transformed with a vector that expresses an antigen, such as a latent virus antigen or a tumor antigen, such that the antigen is expressed and presented via class I MHC by the antigen presenting cell. Preferably, more than about 30% of the antigen presenting cells are transduced; more preferably, more than about 50% of the antigen presenting cells are transduced; still more preferably, more than about 60% of the antigen presenting cells are transduced.

As used herein, "effector cell" refers to the cells of the immune system that mount responses to protect individuals from pathogens, preferably viruses, tumor viruses, and tumors (including viral and non-viral tumors). A preferred effector cell of the invention is a population of cytotoxic T cells and T helper cells that host cellular immunity. The terms B-cell and B-lymphocyte are used interchangeably and synonymously herein. Similarly, the terms T-cell and T-lymphocyte are used interchangeably and synonymously herein.

A molecule is "antigenic" when it is capable of specifically interacting with an antigen recognition molecule of the immune system, such as an immunoglobulin (antibody) or T cell antigen receptor. An "immunogenic" molecule is an antigen capable of eliciting an immune response, e.g., a whole protein or organism.

The term "dendritic cell" is used herein to refer to the active antigen presenting cells found in epithelia and thymus-dependent areas of lymphoid tissues. They are characterized by their peculiar dendritic morphology and multiple thin-membrane projections, and by a high density of class II MHC molecules. Dendritic cells include Langerhans cells of the skin, "veiled cells" of afferent lymphatics, follicular dendritic cells, dendritic cells of the spleen, and interdigitating cells of lymphoid organs. Dendritic cells can be obtained from the skin, spleen, bone marrow, or other lymphoid organs, lymph nodes, or blood. Preferably, dendritic cells are obtained from blood or bone marrow for use as APCs of the invention.

As used herein, the term "cancer" refers to sarcomas and carcinomas that are known or found to express the cancer-testis antigen Sp17, and could include, for example: fibrosarcoma, myxosarcoma, lipbsarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The results herein are directed to the cancer referred to as multiple myeloma (MM).

The results herein identify Sp17 (SEQ ID NO:1) as a novel CT antigen in MM. Therefore, studies were done to determine whether Sp7-specific CTL could be generated from the PBMC of a healthy previously unimmunized donor. In addition, studies were done to determine the relevance of these CTL in the context of killing of Sp17+ tumor cells, since this information would provide insight into whether Sp17 is processed, not only by normal cells pulsed with the recombinant protein, but also by Sp17-producing tumor cells. Most importantly, the results of these investigations provide the rationale and basis for the generation of donor-derived Sp17-specific CTL for donor lymphocyte infusion following allogeneic stem cell transplantation to augment GVM without eliciting GVHD.

Initially, Sp17 recombinant protein was generated from *E. coli*. This was achieved through the cloning of the Sp17 cDNA as a fusion gene to produce a recombinant Sp17 protein that contained a 6-His tag at the N-terminal of the protein. This strategy was adopted to facilitate the purification of the recombinant protein by affinity column. The recombinant protein derived from *E. coli* was of the expected molecular weight. However, since the Sp17 recombinant protein is bacteria derived, to exclude immune responses due to contaminating bacterial antigens that may be present in the recombinant protein preparation, a control recombinant protein that has also been prepared from *E. coli* lysate was included.

To optimize the conditions for the generation of Sp17-specific CD8+ CTL, DC were chosen to present the Sp17 antigen, since DC are potent antigen-presenting cells capable of priming naive CD8+ T cells. In addition, DOTAP was used to deliver the Sp17 recombinant protein to the DC based since DOTAP is instrumental in the induction of strong and specific CD8+ CTL responses (Santin et al. 1999). A CD8 predominant CTL line was generated that was able to lyse autologous targets in a Sp17-dependent HLA class I-restricted manner.

Although the CTL were able to kill autologous targets pulsed with the recombinant protein, it remained to be determined if tumor cells expressing Sp17 were able to process and present the Sp17 CTL epitopes in vivo. To determine this, a combination of HLA-matched and mismatched antibody-enriched fresh myeloma tumor cells and myeloma cell lines were used as targets for the recombinant protein-propagated CTL. The findings of target cell lysis suggest that the Sp17 protein produced by Sp17+ tumor cells are processed and presented in vivo and that the CTL epitopes are presented in association with HLA class I molecules in a concentration and configuration recognized by recombinant protein-propagated CTL. These results support Sp17 as a candidate antigen for myeloma-specific donor lymphocyte infusion.

Although Sp17 is not as tumor-specific as idiotypes, Sp17 is a highly immunogenic protein. In addition, unlike the idiotypes that are individual specific and thus require a vaccine to be tailor-made, myeloma-specific donor lymphocyte infusion targeting Sp17 could be applicable to any patients with Sp17+ tumors following allogeneic stem cell transplantation.

For additional background on sperm protein 17 (SEQ ID NO:1) see Lea et al. 1996; Lea et al. 1997; O'Rand and Widgren 1994; Lacy and Sanderson 1999; Lea et al. 1995; Wen et al. 1995; Lea et al. 1994; Lea et al. 1993; U.S. Pat. No. 5,480,799; and U.S. Pat. No. 5,820,861 (the contents of each of which are incorporated herein by reference). For additional background in immunotherapy, diagnostic applications and therapeutic applications in general relation to tumor or viral specific antigens, see U.S. Pat. Nos. 5,695,994; 5,962,318; 5,980,896; 6,083,751; 6,165,725; and 6,171,796 (the contents of each of which are incorporated herein by reference).

Materials and Methods

Materials

Two myeloma cell lines were studied (ARP-1 and ARK-B, gifts from J. Epstein, University of Arkansas for Medical Sciences, Little Rock, Ark.) and bone marrow from 13 normal donors and 47 myeloma patients. The degree of bone marrow myeloma involvement ranged from 10% to 80% (in 6 patients, only BB4 antibody-enriched myeloma cells were used). The ARP-1 (HLA-A1; B15, 27; Cw2, Cw3) and ARK-B (HLA-A66, A68; B41, B44; Cw5, Cw17) cell lines were established from bone marrow aspirate of patients with MM. Peripheral blood mononuclear cells (PBMC) were obtained from a healthy male (previously unvasectomized) and a healthy female donor. The HLA phenotypes of these donors were: donor 1 (HB001) (HLA-A1; B44, B27; Cw2); donor 2 (HB002) (HLA-A24, A11; B7, B14; Cw7); donor 3 (HB003) [HLA-A1, A3; B8, B56 (22)]; donor 4 (HB004) [HLA-A2, A11; B55 (22), B61 (40)]. Anti-Syndecan-1 (CD138) antibody-sorted tumor cells were obtained from three patients with MM. The HLA phenotypes of these patients were: Patient 1 (HLA-A1, A11; B8, B18; Cw7); Patient 2 (A1, A2; B7, B8; Cw7) and Patient 3 (HLA-A1, A11; B51, B44; Cw5). All clinical materials were obtained with the patients' consents and approval from the local ethics committee. Polyclonal rabbit antisera against human Sp17 protein was kindly provided by Michael O'Rand (University of North Carolina, Chapel Hill, N.C.).

Reverse Transcription-polymerase Chain Reaction

Total RNA was extracted from cells by means of the Tri-reagent (Sigma, St Louis, Mo.). All RNA specimens were first treated with DNAse I (Ambion, Austin, Tex.) to remove genomic DNA contamination. First strand cDNA was synthesized from 1 µg of total RNA by means of random hexamer primer. PCR was used to amplify a complementary DNA (cDNA) of approximately 500 base pairs (bp). PCR was performed by means of 35 amplification cycles at an annealing temperature of 55° C. Positive control amplification contained a plasmid with the Sp17 cDNA and a negative control of the PCR reaction mixture except for substitution of cDNA by water. RNA integrity in each sample was checked by amplification of a GAPDH gene segment. Successful removal of genomic DNA contamination was confirmed in each sample by amplification of the RNA without prior reverse-transcription (RT) reaction. PCR products were visualized on an ethidium bromide agarose gel for a DNA band of the expected size. All results were confirmed in 2 independent RT-PCRs.

Northern Blot Analysis

15 µg of total RNA from each normal tissue was electrophoresed (Invitrogen, Leeks, The Netherlands) on a 1.2% agarose/formaldehyde gel and transferred onto a nitrocellulose membrane. Subsequent hybridization to a $^{32}$P-labeled probe (derived from a plasmid containing the full-length Sp17 cDNA) and washing were performed under high-stringency conditions. Hybridization was performed at 60° C. overnight, and final washes of the membranes were performed at 60° C. with 0.1×SSC in 0.1% sodium dodecyl sulfate (SDS) solution.

Western Blot Analysis

Lysates from tumor cells and cells from normal donor marrow were fractionated in a 12% SDS-polyacrylamide gel and transferred onto a nitrocellulose membrane. Sp17 protein was detected by rabbit polyclonal anti-Sp17 antibody followed by an alkaline phosphatase-conjugated goat anti-rabbit immunoglobulin G antibody. Antibody binding was visualized by reaction with the Western blue stabilized substrate (Promega).

Flow Cytometric Analysis

This was carried out on myeloma cell lines by means of a FACScan. Rabbit polyclonal anti-Sp17 antibody was used, and 2-stage indirect staining was carried out.

Generation and Purification of Sp17 Recombinant Protein

Full-length Sp17 cDNA was isolated and amplified from normal testicular RNA by RT-PCR. Following gel purification of the PCR products, the cDNA was cloned into pQE30 vector (Qiagen, USA) at BamHI and HindIII, transformed into *E. coli* TOP 10F' strain and selected on agar plates for ampicillin resistance. The Sp17 cDNA was therefore cloned and expressed as a fusion protein with an N-terminal 6-His tag. Recombinant clones were sequenced bi-directionally and the recombinant protein produced in *E. coli* by bacterial lysis and purified in a Ni-NTA column. Successful generation of Sp17 recombinant protein was confirmed on SDS-PAGE and Western blot analysis.

Isolation of PBMC and Generation of DC

PBMC were separated from heparinized venous blood by Ficoll-Hypaque (Sigma) density gradient centrifugation. DC were generated from peripheral blood monocytes as previously described (Lim and Bailey-Wood 1999; Wen et al. 1998). Briefly, PBMC were seeded into six-well culture plates containing 3 ml of RPMI 1640 and 10% FCS at $5\times10^6$ to $10\times10^6$/well. After 2 h at 37° C., nonadherent cells were removed and the adherent cells were cultured at 37° C. in RPMI 1640 supplemented with 10% FCS, 800 IU/ml GM- CSF (Immunex, Seattle, Wash.) and 1,000 IU/ml IL-4 (Genzyme, Cambridge, Mass.). After 7 days of culture, DC were harvested for pulsing with Sp17 recombinant protein.

DC Pulsing

Following culture, DC were washed twice and added to 50-ml polypropylene tubes. The cationic lipid DOTAP (Boehringer Mannheim Biochemicals, Indianapolis, Ind.) was used to deliver the Sp17 recombinant protein because it was previously found that DC with DOTAP-delivered antigens efficiently promoted CD8 responses (Santin et al. 1999). Briefly, the recombinant protein was mixed with the lipid at room temperature for 20 min and added to DC at 37° C. in an incubator with occasional agitation for 3 h. The cells were washed twice before being used as antigen-presenting cells.

In Vitro Generation of SD17-Specific CTL

Fresh PBMC were co-cultured with antigen-pulsed DC at a ratio of 10:1 in RPMI 1640 supplemented with 10% autologous serum, IL-2 (10 IU/ml) and IL-7 (5 ng/ml) and incubated at 37° C. IL-2 was added to the culture every 3 to 4 days thereafter. Irradiated autologous PBMC feeder cells and Sp17 recombinant protein (50 µg/ml) was added to the culture every week. The cells were harvested after four rounds of stimulation and used for cytotoxicity assays.

Cytotoxicity Assays

Standard 4-hour $^{51}$Cr-release assays were performed as previously described (Santin et al. 1999) to determine the cytotoxic activity of the Sp17-stimulated T cells. Target cells (at an E:T ratio of 20:1) used included autologous EBV-transformed LCL, HLA-mismatched donor LCL, ARP-1 cells, ARK-B cells, K562 cells and CD138 antibody-enriched tumor cells from three patients with MM. To determine the HLA dependency of the cytotoxicity, the following antibodies were added to the co-cultures: HLA class I (W6/32) and HLA class II (L243) at a concentration of 25 µg/ml, and HLA-A1 and HLA-B27 antisera (at a final concentration of 1:4). For all targets (including fresh myeloma cells), the maximum releases were in excess of 2,000 cpm and the spontaneous release <30% of the maximum release.

Flow Cytometric Analysis of Intracellular Cytokines

This was carried out as previously described (Santin et al. 1999). Briefly, the T cell population was tested 4 weeks after priming, after resting for 6 days following the last antigen stimulation. The T cells were incubated at 37° C. for 6 h in RPMI 1640 plus 10% FCS, 50 µg/ml of Sp17 recombinant protein and 500 ng/ml ionomycin. Brefeldin A (10 µg/ml) was added for the final 3 h of incubation. Controls (non-activated cultures) were incubated in the presence of Brefeldin A only. The cells were harvested, washed, and fixed with 2% paraformaldehyde in PBS for 20 min at room temperature, after which they were washed and stored overnight in PBS at 4° C. For intracellular staining, the cells were washed and permeabilized by incubation in PBS plus 1% bovine serum albumin and 0.5% saponin (Sigma) for 10 min at room temperature. Activated and control cells were stained with fluorescein isothiocyanate (FITC)-labeled anti-IFN-γ, phycoerythrin (PE)-labeled anti-IL-4, and isotype-matched control antibodies (Becton Dickinson) and analyzed by flow cytometry.

EXAMPLE I

Using a pair of sequence-specific primers, the presence of Sp17 messenger RNA (mRNA) in 2 out of 2 myeloma cell lines and 7 of 41 (17%) total RNA samples from fresh unfractionated myeloma bone marrow was demonstrated. In another 6 bone marrow specimens obtained from myeloma patients, myeloma cells were purified with the use of the BB4 antibodies (directed at syndecan-1 expressed on myeloma cells); Sp17 transcripts were detected in 5 of these 6 specimens. In contrast, Sp17 mRNA was not detected in the bone marrow from any of the 13 normal healthy donors (Fisher exact test, P=0.05). To confirm that the Sp17 mRNA resulted in the production of the Sp17 protein, the 6 BB4 antibody-purified fresh myeloma cells and ARK myeloma cell lines were also used for Western blot analysis. Sp17 protein was detected in all of the 5 BB4-enriched specimens that were also positive by RT-PCR and in the ARK cell line but not detected in either of the 2 normal bone marrows. These results therefore suggest that Sp17 is expressed, at both the mRNA and the protein level, in myeloma cells but not in normal bone marrow. It is likely that the prevalence of Sp17 expression in myeloma is underestimated by RT-PCR of total RNA derived from unfractionated bone marrow because of the relative low mRNA copy number within the myeloma cells that are actively synthesizing high levels of idiotypic protein. The detection may, however, be increased by enrichment of the tumor cell population.

Since tissue specificity is a vital consideration in the choice of an antigen for immunotherapy, the expression of Sp17 transcripts in a panel of normal tissue RNA was determined. Positive signals of approximately 1.3 kilobases (kb) were detected strongly only in normal testis and weakly in normal prostate. By RT-PCR, low copy number expression in these normal tissues was excluded and it was shown that the transcripts were detected only in normal testis (confirming the restricted normal tissue distribution of the Sp17 transcripts). Although the PCR was not designed primarily to give accurate mRNA quantitation, the reproducibly weaker signal from Sp17-positive myeloma cells when compared with those obtained with normal testicular PCR products suggests a lower level of Sp17 expression in myeloma cells. Sp17 may therefore be a suitable molecule for T-cell targeting in myeloma. Sp17 is also expressed on the 2 myeloma cell lines as a surface protein and may therefore be a suitable surface antigen for antibody targeting.

EXAMPLE II

Production of Purified Sp17 Recombinant Protein from *E. coli*

To produce the recombinant Sp17 protein, the full-length coding sequence of Sp17 cDNA was first isolated and amplified by reverse transcription (RT)-PCR from normal testicular RNA. The cDNA was cloned directionally into the pQE30 vector to produce a recombinant fusion protein of Sp17 that contained a 6-His peptide at the N-terminal of the protein. This strategy was chosen to allow affinity purification of the recombinant protein in a Ni-Sephadex column. In addition, the 6-His tag was chosen instead of another N-terminal tag because the 6-His tag is generally poorly immunogenic; therefore, it would not be expected to contribute to the immunogenicity of the fusion protein. A recombinant clone was expanded in liquid culture and the recombinant Sp17 protein harvested from *E. coli* lysate. Successful production of Sp17 recombinant protein was demonstrated in Western blot analysis, showing binding of the Sp17 polyclonal rabbit antisera to a protein of the expected size of around 25 kDa. Following passage through the Ni-NTA affinity column and numerous rounds of washing, the protein was eluted and the purity of the recombinant protein checked in SDS-PAGE by Coomassie blue staining that indicated a protein purity in excess of 95%. The protein was diluted in phosphate-buffered saline and stored at −20° C. until being used.

EXAMPLE III

Successful Generation of HLA-Class I Restricted Sp17-Specific CTL

Since Sp17 is a highly immunogenic protein, and since more than 90% of normal men who undergo vasectomy spontaneously develop immune responses against Sp17 protein, CTL were generated from the PBMC of a previously unvasectomized male to determine the ability of the recombinant protein to induce a primary immune response. Using autologous DC pulsed with Sp17 recombinant protein, Sp17-specific CTL were successfully generated after three rounds of T cell stimulation with the recombinant protein. When used as effector cells in cytotoxicity assays, these T cells were able to efficiently kill an autologous lymphoblastoid cell line (LCL) pulsed with the Sp17 recombinant protein. Target lysis for the autologous LCL was Sp17 dependent since a significantly lower cytotoxicity was observed when the autologous LCL pulsed with a control *E. coli*-derived recombinant protein, generated using an identical method to that used for the generation of Sp17 recombinant protein, was used as target in the cytotoxicity assays ($p<0.0001$). This result therefore indicates that recombinant Sp17 protein when used with autologous DC can prime T cells, and supports the successful generation of Sp17-specific CTL using autologous DC and recombinant Sp17 protein. Target lysis was not mediated by Natural Killer (NK) cells, because no cytotoxicity was observed when K562 cells were used as target cells in this study. Target lysis was, however, HLA class I restricted, and could be blocked by antibodies directed against monomorphic HLA class I molecules. In contrast, HLA class II antibodies did not affect the cytotoxic activity of the T cells ($p<0.00001$). These results point to the involvement of CD8 T cells in the CTL activity against Sp17-pulsed autologous target cells. Class I involvement in the CTL activity was further delineated and localized to HLA-A1 and HLA-B27 molecules on the target cells, since both antibodies could each partially block the target killing ($p<0.00001$). Blocking by antibody against either HLA-A1 or HLA-B27 individually was significantly lower than that obtained using antibodies against monomorphic HLA class I molecules. The HLA class I restriction of these CTL was also further confirmed by the ability of the CTL to kill HLA-matched donor LCL in an Sp-17-dependent manner and an inability to kill HLA-mismatched Sp17-pulsed LCL targets.

EXAMPLE IV

Recombinant Protein-Primed CTL Lyse Sp17$^+$ HLA Class I-Matched Tumor Cells

To investigate the feasibility of using donor-derived Sp17-specific CTL to augment GVM, the relevance of the Sp17-primed donor CTL in the context of tumor cell lysis was investigated. RT-PCR was used to confirm that all the five cell types used were Sp17$^+$. These five Sp17$^+$ HLA class I-matched and -mismatched myeloma tumor cells (fresh tumor cells from three myeloma patients, ARK-B cells and ARP-1 cells) were then used as target cells in the standard $^{51}$Cr-release assays. Target killing was observed in all three HLA-A1$^+$ fresh myeloma cells and the HLA-A1$^+$ and HLA-B27$^+$ ARP-1 cells. No target lysis was observed with ARK-B cells that were HLA class I mismatched, despite the cells being Sp17$^+$. The results therefore suggest the in vivo processing and presentation of Sp17 CTL peptides in association with the HLA-A1 and HLA-B27 molecules in Sp17$^+$ tumor cells. Furthermore, they also demonstrate that Sp17 recombinant protein can be used to prime and propagate CTL that recognize Sp17 peptides at a concentration and configuration similar to those presented on the surface of Sp17$^+$ tumor cells.

EXAMPLE V

Phenotypes and Cytokine Profiles of CTL Line

Flow cytometry was used to evaluate the phenotype of the generated CTL line. Compared to unstimulated PBMC from the same donor, there was a predominance of CD8$^+$ T cells, and a paucity of CD4$^+$ T cells, in the CTL line. These T cells were mainly CD56$^-$. Taken together with the results of the cytotoxicity assays, these results support the involvement of CD8$^+$ T cells in the CTL activities. Two-color flow cytometric analysis for intracellular IFN-γ and IL-4 following Sp17 recombinant protein restimulation of the T cells was carried out to determine the cytokine profile of the CTL line. As expected, the CTL line produced predominantly IFN-γ and very little IL-4, a pattern in keeping with a Th1 cytokine profile. This cytokine profile was observed in both the CD4-enriched and CD8-enriched T cell populations in the CTL line.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Corradini et al. 1993. Blood 15: 2708-2713.

Desikan et al. 2000. Blood 95: 4008-4010.

Lacy and Sanderson. 1999. Mol Biol Cell 10(Suppl): 459a, abstract no. 2655.

Lea et al. 1993. Mol Cell Biol 4(Suppl): 248A, abstract no. 1439.

Lea et al. 1994. J Reproduction & Fertility Abstracts Series 0(14): 9, abstract no. 18.

Lea et al. 1995. Mol Biol Cell 6(Suppl): 429A, abstract no. 2497.

Lea et al. 1996. Biochimica et Biophysica Acta 1307: 263-266.

Lea et al. 1997. Fertil Steril 67: 355-361.

Lea et al. 1998. Biol Reprod 59: 527-536.

Lim and Bailey-Wood. 1999. Int J Cancer 83: 215-222.

Lim et al. 1999. Br J Cancer 81: 1162-1164.

Massaia et al. 1999. Blood 94: 673-683.

Noto et al. 1997. Int Immunol 9: 791-798.

Olds and Chen. 1998. J Exp Med 187: 1163-1167.

O'Rand and Widgren. 1994. Reprod Fertil Dev 6: 289-296.

Osterborg et al. 1999. Blood 91: 2459-2466.

Reichardt et al. 1999. Blood 93: 2411-2419.

Santin et al. 1999. J Virol 73: 5402-5410.

Van Baren et al. 1999. Blood 94: 1156-1164.

Wen et al. 1995. Mol Biol Cell 6(Suppl): 320A, abstract no. 1860.

Wen et al. 1998. Clin Cancer Res 4: 957-962.

What is claimed is:

1. An isolated cytotoxic T cell which specifically recognizes the human sperm protein 17 (Sp17) encoded by SEQ ID NO:1.

* * * * *

SEQUENCE LISTING

<160> NUMBER OF SEQ ID NOS: 1

<210> SEQ ID NO 1
<211> LENGTH: 151
<212> TYPE: PRT
<213> ORGANISM: Homo sapiens

<400> SEQUENCE: 1

```
Met Ser Ile Pro Phe Ser Asn Thr His Tyr Arg Ile Pro Gln Gly Phe
 1               5                  10                  15

Gly Asn Leu Leu Glu Gly Leu Thr Arg Glu Ile Leu Arg Glu Gln Pro
            20                  25                  30

Asp Asn Ile Pro Ala Phe Ala Ala Tyr Phe Glu Ser Leu Leu Glu
        35                  40                  45

Lys Arg Glu Lys Thr Asn Phe Asp Pro Ala Glu Trp Gly Ser Lys Val
    50                  55                  60

Glu Asp Arg Phe Tyr Asn Asn His Ala Phe Glu Gln Glu Pro Pro
 65                  70                  75                  80

Glu Lys Ser Asp Pro Lys Gln Glu Glu Ser Gln Ile Ser Gly Lys Glu
                85                  90                  95

Glu Glu Thr Ser Val Thr Ile Leu Asp Ser Ser Glu Glu Asp Lys Glu
            100                 105                 110

Lys Glu Glu Val Ala Ala Val Lys Ile Gln Ala Ala Phe Arg Gly His
        115                 120                 125

Ile Ala Arg Glu Glu Ala Lys Lys Met Lys Thr Asn Ser Leu Gln Asn
    130                 135                 140

Glu Glu Lys Glu Glu Asn Lys
145                 150
```